(12) United States Patent
Kuroda et al.

(10) Patent No.: US 6,872,331 B2
(45) Date of Patent: Mar. 29, 2005

(54) OXIDE ION CONDUCTOR, MANUFACTURING METHOD THEREFOR, AND FUEL CELL USING THE SAME

(75) Inventors: Kiyoshi Kuroda, Omiya (JP); Takashi Yamada, Omiya (JP); Yoshitaka Tamo, Omiya (JP); Kazunori Adachi, Omiya (JP)

(73) Assignee: Mitsubishi Materials Corporation, Tokyo (JP)

( * ) Notice: Subject to any disclaimer, the term of this patent is extended or adjusted under 35 U.S.C. 154(b) by 0 days.

(21) Appl. No.: 10/632,824

(22) Filed: Aug. 4, 2003

(65) Prior Publication Data

US 2004/0026668 A1 Feb. 12, 2004

Related U.S. Application Data

(63) Continuation of application No. 09/797,595, filed on Mar. 5, 2001, now abandoned.

(30) Foreign Application Priority Data

| Mar. 15, 2000 | (JP) | ........................................ 2000-071759 |
| Jul. 14, 2000 | (JP) | ........................................ 2000-213659 |

(51) Int. Cl.$^7$ .......................... C04B 35/50; H01M 8/12; G01N 27/12; B01J 20/28
(52) U.S. Cl. ................. 252/518.1; 252/500; 252/519.1; 429/33; 429/44; 502/4; 204/421; 501/10; 501/134
(58) Field of Search .............................. 252/500, 518.1; 429/33, 30, 44; 502/4; 204/421; 501/10, 134

(56) References Cited

U.S. PATENT DOCUMENTS 6,090,500 A * 7/2000 Ishihara et al. ................ 429/33

| 6,287,716 | B1 | * | 9/2001 | Hashimoto et al. | ............ 429/33 |
| 6,337,006 | B1 | * | 1/2002 | Fujita et al. | ................. 204/421 |
| 6,586,127 | B1 | * | 7/2003 | Ishihara et al. | ............... 429/33 |
| 6,635,376 | B2 | * | 10/2003 | Hashimoto et al. | ............ 429/33 |

FOREIGN PATENT DOCUMENTS

| JP | 19839382 A1 | * | 3/1999 | ............. C01G/1/02 |
| JP | 11-335164 | | * 12/1999 | .......... C04B/35/495 |

OTHER PUBLICATIONS

Ishihara et al, "Improved oxide ionic conductivity in La0.8Sr0.2Ga0.8Mg0.2O3 by doping Co", Chem. Mater, 1999, 11(8),2081–2088.*
Keppeler et al, "Mixed conductivity in Co–doped lanthanum gallate", J. Australasian Ceramic Society, 1998, 34(1), 106–111.*
Tas et al, "Chemical Preparation of Pure and Strontium– and/or Magnesium–Doped Lanthanum Gallate Powders", J. Am. Ceram. Soc. 2000, 83(12), pp 2954–2960.*

* cited by examiner

*Primary Examiner*—Mark Kopec
*Assistant Examiner*—Kallambella Vijayakumar
(74) *Attorney, Agent, or Firm*—Oblon, Spivak, McClelland, Maier & Neustadt, P.C.

(57) ABSTRACT

An oxide ion conductor is manufactured having a relatively high mechanical strength while the ionic conduction thereof is maintained at a satisfactory level. The oxide ion conductor is represented by the formula $Ln1_{1-x}A_xGa_{1-y-z-w}B1_yB2_zB3_wO_{3-d}$. In the oxide ion conductor, Ln1 is at least one element selected from the group consisting of La, Ce, Pr, Nd, and Sm, A is at least one element selected from the group consisting of Sr, Ca, and Ba, B1 is at least one element selected from the group consisting of Mg, Al, and In, B2 is at least one element selected from the group consisting of Co, Fe, Ni, and Cu, and B3 is at least one element selected from the group consisting of Al, Mg, Co, Ni, Fe, Cu, Zn, Mn, and Zr, wherein x is 0.05 to 0.3, y is 0.025 to 0.29, z is 0.01 to 0.15, w is 0.01 to 0.15, y+z+w is 0.035 to 0.3, and d is 0.04 to 0.3.

23 Claims, 5 Drawing Sheets

OXIDE ION CONDUCTOR, MANUFACTURING METHOD THEREFOR, AND FUEL CELL USING THE SAME

This application is a continuation application of U.S. application Ser. No. 09/797,595 filed on Mar. 5, 2001, abandoned.

BACKGROUND OF THE INVENTION

1. Field of the Invention

The present invention relates to oxide ion conductors which are effectively used for electrolytes or air electrodes for fuel cells, gas sensors such as oxygen gas sensors, oxygen separation membranes for electrochemical oxygen pumps and the like, gas separation membranes, and the like.

2. Description of the Related Art

As a typical example of conventional oxide ion conductors, a solid solution having a cubic fluorite system is known as "a stabilized zirconia" in which a small amount of a divalent or a trivalent metal oxide, such as CaO, MgO, $Y_2O_3$, or $Gd_2O_3$, is dissolved in zirconium oxide ($ZrO_2$). A stabilized zirconia has superior heat stability, and in addition, has an advantage in which the ionic transference number (a ratio of oxide ionic conduction to electrical conduction) does not tend to decrease even if the oxygen partial pressure is decreased since the oxide ion conduction is dominant at all oxygen partial pressures from an oxygen atmosphere to a hydrogen atmosphere. Accordingly, a stabilized zirconia is widely used as zirconia (oxygen) sensors for various industrial process controls, such as for steel manufacturing, and for combustion control (an air-fuel ratio) for automobiles. In addition, a stabilized zirconia is also used as an electrolyte for a solid oxide fuel cell (SOFC) under development, which is operated at approximately 1,000° C.

However, the oxide ionic conduction of a stabilized zirconia is not sufficiently high, and in particular, the conduction thereof becomes deficient when a temperature is decreased. For example, the ionic conductivity of $Y_2O_3$— stabilized zirconia is $10^{-4}$ S/cm at 1,000° C. but is decreased to $10^{-4}$ S/cm at 500° C., whereby there is an inconvenient limitation in which the operating temperature must be controlled at a higher temperature, such as 800° C. or more.

In order to solve the problems described above, an oxide ion conductor having a perovskite structure is proposed provided with oxide ionic conduction higher than that of a stabilized zirconia (refer to Japanese Unexamined Patent Application Publication Nos. 11-228136, 11-335164). These oxide ion conductors mentioned above are compound oxides composed of four elements or five elements, and an oxide ion conductor disclosed in Japanese Unexamined Patent Application Publication No. 11-335164 is a substance represented by the formula $Ln_{1-x}A_xGa_{1-y-z}B1_yB2_zO_3$ in which Ln is a lanthanoid rare earth metal, A is an alkaline earth metal, B1 is a non-transition metal, and B2 is a transition metal. That is, this oxide ion conductor has a basic lanthanoid.gallate ($LnGaO_3$) structure and is a compound oxide composed of five elements (Ln+A+Ga+B1+B2) formed by doping three elements, i.e., an alkaline earth metal (A), a non-transition metal (B1), and a transition metal (B2), in the lanthanoid.gallate structure, or is a compound oxide composed of four elements (Ln+A+Ga+B2) formed by doping two elements, i.e., an alkaline earth metal (A), and a transition metal (B2), in the lanthanoid.gallate structure.

The oxide ion conductor described above has oxide ionic conduction higher than that of a stabilized zirconia and has superior heat stability, in which the high oxide ionic conduction thereof can be maintained at a higher temperature and also even at a lower temperature. Furthermore, it is confirmed that the decrease in ionic transference number is preferably small at all oxygen partial pressures from an oxygen atmosphere to a hydrogen atmosphere (i.e., even at a lower oxygen partial pressure), and that oxide ionic conduction is dominant, or mixed ionic conduction is observed.

However, in the oxide ion conductor disclosed in Japanese Unexamined Patent Application Publication No. 11-228136, there is a problem in that the oxide ionic conduction is low, and in the oxide ion conductor disclosed in Japanese Unexamined Patent Application Publication No. 11-335164, there is a problem, which must be overcome, in that the mechanical strength is not sufficient. Since an oxide ion conductor is used in a manner in which gases having different compositions from each other are supplied at the front and the rear surfaces of the oxide ion conductor, respectively, to contact thereon so that reactions occur, when cracks or continuous pores are formed in the oxide ion conductor, the gases at the front and the rear surfaces thereof leak through the cracks or the continuous pores. When the gases leak, the performance of the component is decreased, the efficiency thereof is significantly degraded, and in addition, the entire component may be seriously damaged.

SUMMARY OF THE INVENTION

Accordingly, it is an object of the present invention to provide an oxide ion conductor having a relatively high mechanical strength while the ionic conduction is maintained at a level sufficient in practical use.

An oxide ion conductor of the present invention is represented by the formula Ln1AGaB1B2B3O.

In the oxide ion conductor of the present invention, Ln1 is at least one element selected from the group consisting of La, Ce, Pr, Nd, and Sm, in which the content thereof is 43.6 to 51.2 percent by weight; A is at least one element selected from the group consisting of Sr, Ca, and Ba, in which the content thereof is 5.4 to 11.1 percent by weight; the content of Ga is 20.0 to 23.9 percent by weight; B1 is at least one element selected from the group consisting of Mg, Al, and In; B2 is at least one element selected from the group consisting of Co, Fe, Ni, and Cu; and B3 is at least one element selected from the group consisting of Al, Mg, Co, Ni, Fe, Cu, Zn, Mn, and Zr, wherein, in the case in which B3 is an element differing from B1 or B2, the content of B1 is 1.21 to 1.76 percent by weight, the content of B2 is 0.84 to 1.26 percent by weight, and the content of B3 is 0.23 to 3.08 percent by weight, and in the case in which B3 is an element equal to B1 or B2, the total content of B1 and B3 is 1.41 to 2.70 percent by weight, and the total content of B2 and B3 is 1.07 to 2.10 percent by weight.

An oxide ion conductor of the present invention is represented by the formula $Ln1_{1-x}A_xGa_{1-y-z-w}B1_yB2_zB3_wO_{3-d}$.

In the oxide ion conductor of the present invention described above, Ln1 is at least one element selected from the group consisting of La, Ce, Pr, Nd, and Sm; A is at least one element selected from the group consisting of Sr, Ca and Ba; B1 is at least one element selected from the group consisting of Mg, Al, and In; B2 is at least one element selected from the group consisting of Co, Fe, Ni, and Cu; and B3 is at least one element selected from the group consisting of Al, Mg, Co, Ni, Fe, Cu, Zn, Mn, and Zr, wherein x is 0.05 to 0.3, y is 0.025 to 0.29, z is 0.01 to 0.15, w is 0.01 to 0.15, y+z+w is 0.035 to 0.3, and d is 0.04 to 0.3.

According to the oxide ion conductors of the present invention described above, represented by the formulas Ln1AGaB1B2B3O and Ln1$_{1-x}$A$_x$Ga$_{1-y-z-w}$B1$_y$B2$_z$B3$_w$O$_{3-d}$, the oxide ionic conduction thereof is higher than that of an oxide ion conductor composed of a conventional stabilized zirconia, and the mechanical strength is higher than that of an oxide ion conductor disclosed in Japanese Unexamined Patent Application Publication No. 11-335164, composed of a five-element (Ln+A+Ga+B1+B2) compound oxide or a four-element (Ln+A+Ga+B2) compound oxide.

In the oxide ion conductor represented by the formula Ln1AGaB1B2B3O described above, first crystal grains composed of elements Ln1, A, and Ga and second crystal grains composed of element B1 may be present between matrix crystal grains other than the first crystal grains and the second crystal grains.

In the oxide ion conductor represented by the formula Ln1$_{1-x}$A$_x$Ga$_{1-y-z-w}$B1$_y$B2$_z$B3$_w$O$_{3-d}$ described above, wherein first crystal grains composed of elements Ln1, A, and Ga and second crystal grains composed of element B1 may be present between matrix crystal grains other than the first crystal grains and the second crystal grains.

In the oxide ion conductor represented by the formula Ln1AGaB1B2B3O, described above, the first crystal grains composed of elements Ln1, A, and Ga and the second crystal grains composed of an element B1 may be present in the matrix crystal grains other than the first crystal grains and the second crystal grains.

In the oxide ion conductor represented by the formula Ln1$_{1-x}$A$_x$Ga$_{1-y-z-w}$B1$_y$B2$_z$B3$_w$O$_{3-d}$ described above, the first crystal grains composed of elements Ln1, A, and Ga and the second crystal grains composed of element B1 may be present in the matrix crystal grains other than the first crystal grains and the second crystal grains.

In the present invention, as described above, since the first crystal grains and the second crystal grains may be present between the matrix crystal grains or in the matrix crystal grains, the growth of the matrix crystal grains can be suppressed, and hence, the mechanical strength of the oxide ion conductor can be improved while the ionic conduction thereof is maintained at a level to be required.

In the oxide ion conductor represented by the formula Ln1AGaB1B2B3O according to the present invention, the grain diameters of the first crystal grains and the second crystal grains are preferably 0.1 to 2.0 μm.

In the oxide ion conductor represented by the formula Ln1AGaB1B2B3O according to the present invention, the grain diameter of the matrix crystal grains is preferably 2.0 to 7.0 μm.

In the oxide ion conductor represented by the formula Ln1$_{1-x}$A$_x$Ga$_{1-y-z-w}$B1$_y$B2$_z$B3$_w$O$_{3-d}$ according to the present invention, the grain diameters of the first and the second crystal grains are preferably 0.1 to 2.0 μm.

In the oxide ion conductor represented by the formula Ln1$_{1-x}$A$_x$Ga$_{1-y-z-w}$B1$_y$B2$_z$B3$_w$O$_{3-d}$ according to the present invention, the grain diameter of the matrix crystal grains is preferably 2.0 to 7.0 μm.

In the oxide ion conductors represented by the formula Ln1AGaB1B2B3O and represented by the formula Ln1$_{1-x}$A$_x$Ga$_{1-y-z-w}$B1$_y$B2$_z$B3$_w$O$_{3-d}$ according to the present invention, the growth of the matrix crystal grains can be effectively suppressed so as to sufficiently improve the mechanical strength of the oxide ion conductor.

A method for manufacturing an oxide ion conductor represented by the formula Ln1AGaB1B2B3O according to the present invention, comprises a step of mixing individual powdered oxides composed of Ln1, A, Ga, B1, and B2 in accordance with the ratios described above so as to form a first powdered mixture, a step of calcining the first powdered mixture at 500 to 1,300° C. for 1 to 10 hours so as to form calcined powder; a step of mixing the powdered oxide composed of B3 with calcined powder in accordance with the ratio described above so as to form a second powdered mixture; a step of molding the second powdered mixture so as to form a molded body having a predetermined shape; and a step of baking the molded body for sintering at 1,200 to 1,600° C. for 0.5 to 20 hours.

A solid oxide fuel cell according to the present invention is provided with an electrolyte comprising one of the oxide ion conductors represented by the formulas Ln1AGaB1B2B3O and Ln1$_{1-x}$A$_x$Ga$_{1-y-z-w}$B1$_y$B2$_z$B3$_w$O$_{3-d}$.

A gas sensor according to the present invention comprises one of the oxide ion conductors represented by the formulas Ln1AGaB1B2B3O and Ln1$_{1-x}$A$_x$Ga$_{1-y-z-w}$B1$_y$B2$_z$B3$_w$O$_{3-d}$.

An oxygen separation membrane for use in an electrochemical oxygen pump according to the present invention comprises one of the oxide ion conductors represented by the formulas Ln1AGaB1B2B3O and Ln1$_{1-x}$A$_x$Ga$_{1-y-z-w}$B1$_y$B2$_z$B3$_w$O$_{3-d}$.

In the present invention, the "oxide ion conductor" means a narrowly defined oxide ion conductor in which the electrical conduction is dominantly performed by the oxide ionic conduction. That is, a material is not included in the oxide ion conductor, which is called an electron-ion mixed conductor or an oxide ion mixed conductor, in which the electronic conduction and the ionic conduction serve important roles in electrical conduction.

DESCRIPTION OF THE PREFERRED EMBODIMENTS

Figure 1:
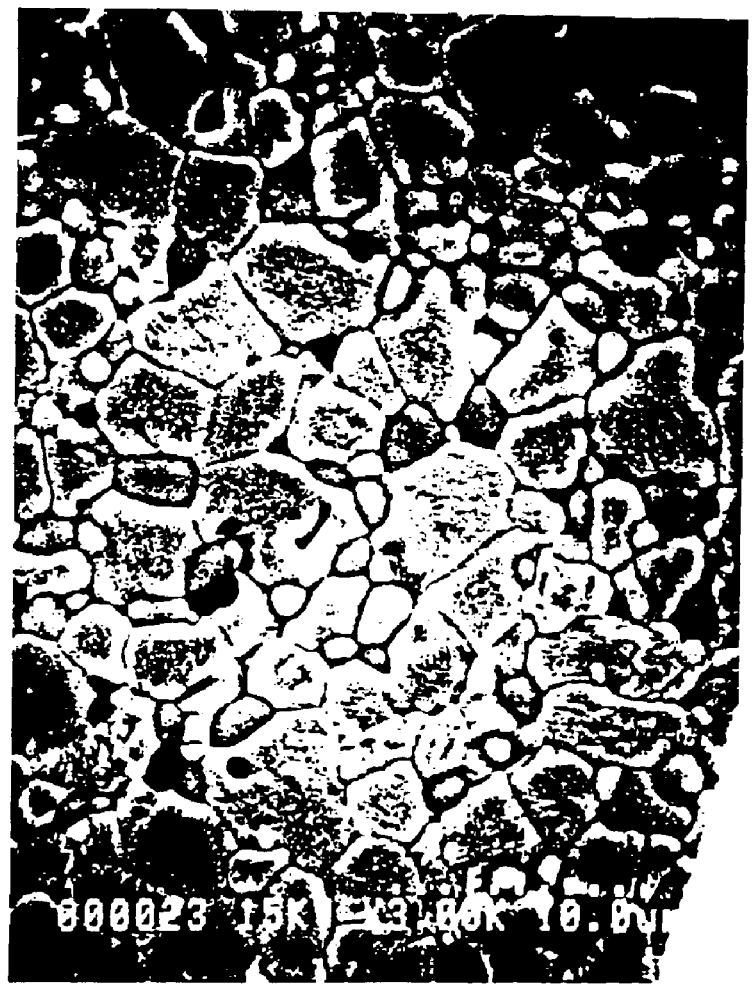
FIG. 1 is a SEM photograph of an oxide ion conductor of Example 4, which is composed of LSGMC mixed with 2 percent by weight of Al$_2$O$_3$.

Next, the embodiments of the present invention will be described.

An oxide ion conductor of the present invention is represented by the formula (1) shown below.

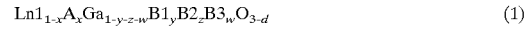

$$Ln1_{1-x}A_xGa_{1-y-z-w}B1_yB2_zB3_wO_{3-d} \qquad (1)$$

In the formula (1) shown above, Ln1 is a lanthanoid rare earth metal element and is at least one selected from the group consisting of La, Ce, Pr, Nd, and Sm. A is an alkaline earth metal and is at least one element selected from the group consisting of Sr, Ca, and Ba. B1 is a non-transition metal and is at least one element selected from the group consisting of Mg, Al, and In. B2 is a transition metal and is at least one element selected from the group consisting of Co, Fe, Ni, and Cu. B3 is a metal added for improving the mechanical strength and is at least one element selected from the group consisting of Al, Mg, Co, Ni, Fe, Cu, Zn, Mn, and Zr. That is, the oxide ion conductor of the present invention has a basic lanthanoid.gallate ($LnGaO_{3-d}$) structure and is a compound oxide composed of six elements (Ln+A+Ga+B1+B2+B3) formed by doping four elements, i.e., the alkaline earth metal (A), the non-transition metal (B1), the transition metal (B2), and the metal (B3) for improving the mechanical strength, in the oxide ion conductor.

In addition, the oxide ion conductor represented by the formula (1) has a perovskite crystal structure, in which A sites of the perovskite structure represented by $ABO_{3-d}$ are occupied by the elements Ln and A of the formula (1), and B sites are occupied by the elements Ga, B1, and B3. Since some of the A sites and the B sites, which are naturally occupied by trivalent metals, are occupied by divalent metals (for example, the element A occupying the A sites and the element B occupying the B sites) and the transition metal (the element B2 occupying the B sites), oxygen holes are produced, whereby oxide ionic conduction is generated by the presence of the oxygen holes. Accordingly, oxygen atoms are decreased corresponding to the number of oxygen holes produced. On the other hand, since excessive elements are kicked out from a matrix crystal grain by adding metal B3, the crystal grain becomes smaller, and hence, the mechanical strength of the oxide ion conductor is improved.

The x in the formula (1) is an atomic ratio of the element A and is set to be 0.05 to 0.3, and preferably, 0.10 to 0.25. The y is an atomic ratio of the element B1 and is set to be 0.025 to 0.29, and preferably, 0.05 to 0.2. The z is an atomic ratio of the element B2 and is set to be 0.01 to 0.15, and preferably, 0.03 to 0.1. The w is an atomic ratio of the element B3 and is set to be 0.01 to 0.15, and preferably, 0.03 to 0.1. The (y+z+w) is set to be 0.035 to 0.3, and preferably, 0.10 to 0.25. The reason the x is set to be 0.05 to 0.3 is that when the x is out of the range mentioned above, the electrical conduction is decreased. The reason the z is set to be 0.01 to 0.15 is that the transference number (ratio of oxide ionic conduction) is decreased concomitant with the increase in z even though the electrical conduction is increased, and hence, the range mentioned above is an optimum range. The reason the w is set to be 0.01 to 0.15 is that the transference number (ratio of oxide ionic conduction) is decreased concomitant with the increase in w even though the mechanical strength is increased, and hence, the range mentioned above is an optimum range. The reason the (y+z+w) is set to be 0.035 to 0.3 is that the transference number is decreased concomitant with the increase in (y+z+w) even though the electrical conduction is increased, and hence, the range mentioned above is an optimum range.

The d is set to be 0.04 to 0.3. The reason the atomic ratio of oxygen is represented by (3-d) in the formula (1) (the actual atomic ratio of oxygen is 3 or less) is that since the number of oxygen holes changes according to temperature, oxygen partial pressure, type of B2 element, and the amount thereof, in addition to types of elements added (A, B1, B2, and B3), the atomic ratio of oxygen is difficult to represent accurately. In this connection, when Co, Fe, Ni, or Cu is used as the element B2, high electrical conduction is observed at a lower temperature side (approximately 650° C.).

When the oxide ion conductor described above is represented by atoms, the oxide ion conductor can be represented by the formula Ln1AGaB1B2B3O. In the formula above, Ln1 is at least one element selected from the group consisting of La, Ce, Pr, Nd, and Sm, and the content thereof is 43.6 to 51.2 percent by weight; A is at least one element selected from the group consisting of Sr, Ca, and Ba, and the content thereof is 5.4 to 11.1 percent by weight; and the content of Ga is 20.0 to 23.9 percent by weight. In addition, B1 is at least one element selected from the group consisting of Mg, Al, and In, B2 is at least one element selected from the group consisting of Co, Fe, Ni, and Cu, and B3 is at least one element selected from the group consisting of Al, Mg, Co, Ni, Fe, Cu, Zn, Mn, and Zr. In the case in which B3 is an element differing from B1 or B2, the content of B1 is 1.21 to 1.76 percent by weight, the content of B2 is 0.84 to 1.26 percent by weight, and the content of B3 is 0.23 to 3.08 percent by weight. On the other hand, in the case in which B3 is an element equal to B1 or B2, the total content of B1 and B3 is 1.41 to 2.70 percent by weight, and the total content of B2 and B3 is 1.07 to 2.10 percent by weight.

The oxide ion conductor of the present invention can be manufactured by a process comprising steps of mixing well individual oxides having component elements at a predetermined mixing ratio, molding the mixture thus formed by an appropriate method, and baking the molded mixture for sintering. As powdered starting materials, in addition to the oxides, precursors (for example, carbonates, and carboxylic acids and the derivatives thereof) can be used which are converted into oxides by pyrolysis. As a preferable method for molding the mixture, a doctor blade method may be mentioned. The baking temperature for sintering is 1,200° C. or more, and preferably, 1,300° C. or more, and the baking time ranges from several hours to several tens of hours. In order to shorten the baking time, pre-baking may be performed at a temperature lower than the sintering temperature of the mixture of the starting materials. For example, the pre-baking may be performed at 500 to 1,300° C. for 1 to 10 hours. The pre-baked mixture is molded after a step of pulverizing when necessary and is finally sintered. Various molding methods may be optionally used, such as uniaxial compression molding, isostatic pressing, extrusion molding, and tape casting. Baking including pre-baking is preferably performed in an oxidative atmosphere, such as in the air, or in an inert gas atmosphere.

That is, a preferable method for manufacturing the oxide ion conductor comprises steps of mixing individual powdered oxides including component elements Ln1, A, Ga, B1, and B2 at a predetermined mixing ratio so as to form a first powdered mixture, calcining the first powdered mixture at 500 to 1,300° C. for 1 to 10 hours so as to form calcined powder, mixing a powdered oxide including the element B3 with the calcined powder at a predetermined mixing ratio so as to form a second powdered mixture, molding the second powdered mixture into a molded body having a predetermined shape, and baking the molded body for sintering at 1,200 to 1,600° C. for 0.5 to 20 hours.

In the oxide ion conductor thus sintered, first crystal grains composed of Ln1, A, and Ga, and second crystal grains composed of B1 are present between matrix crystal grains other than the first and the second crystal grains. That is, the first crystal grains are composed of at least one element selected from the group consisting of La, Ce, Pr, Nd, and Sm, at least one element selected from the group consisting of Sr, Ca, and Ba, and Ga; and the second crystal grains are composed of at least one selected from the group consisting of Mg, Al, and In. The matrix crystal grains are crystal grains other than the first and the second crystal grains. Since the first and the second crystal grains are present between the matrix crystal grains or are present therein, the growth of the matrix crystal grains is suppressed, and hence, the diameter of the matrix crystal grains are smaller compared to that of conventional crystal grains which do not have the first and the second crystal grains, whereby the mechanical strength can be improved. The grain diameters of the first and the second crystal grains are preferably 0.1 to 2.0 μm, and the volume fractions of the first and the second crystal grains are preferably 0.5 to 20 percent by volume. The grain diameter of the first crystal grains is more preferably 0.5 to 2.0 μm, and the volume fraction thereof is more preferably 1 to 10 percent by volume. The grain diameter of the matrix crystal grains, the growth of which is suppressed, is preferably 2.0 to 7.0 μm.

In the oxide ion conductor of the present invention, the oxide ionic conduction is dominant in the electrical conduction (that is, the ionic transference number is 0.7 or more), and the oxide ion conductor of the present invention is a narrowly defined oxide ion conductor. This material can be used for applications (for example, electrolytes for solid oxide fuel cells, and gas sensors) of various oxide ion conductors, in which a stabilized zirconia is conventionally used. Since this type of oxide ion conductor of the present invention has higher oxide ionic conduction than that of a stabilized zirconia and is functional at a lower temperature, it is believed that products having superior performance can be manufactured by using this material than those manufactured by using a conventional stabilized zirconia.

Figure 5:
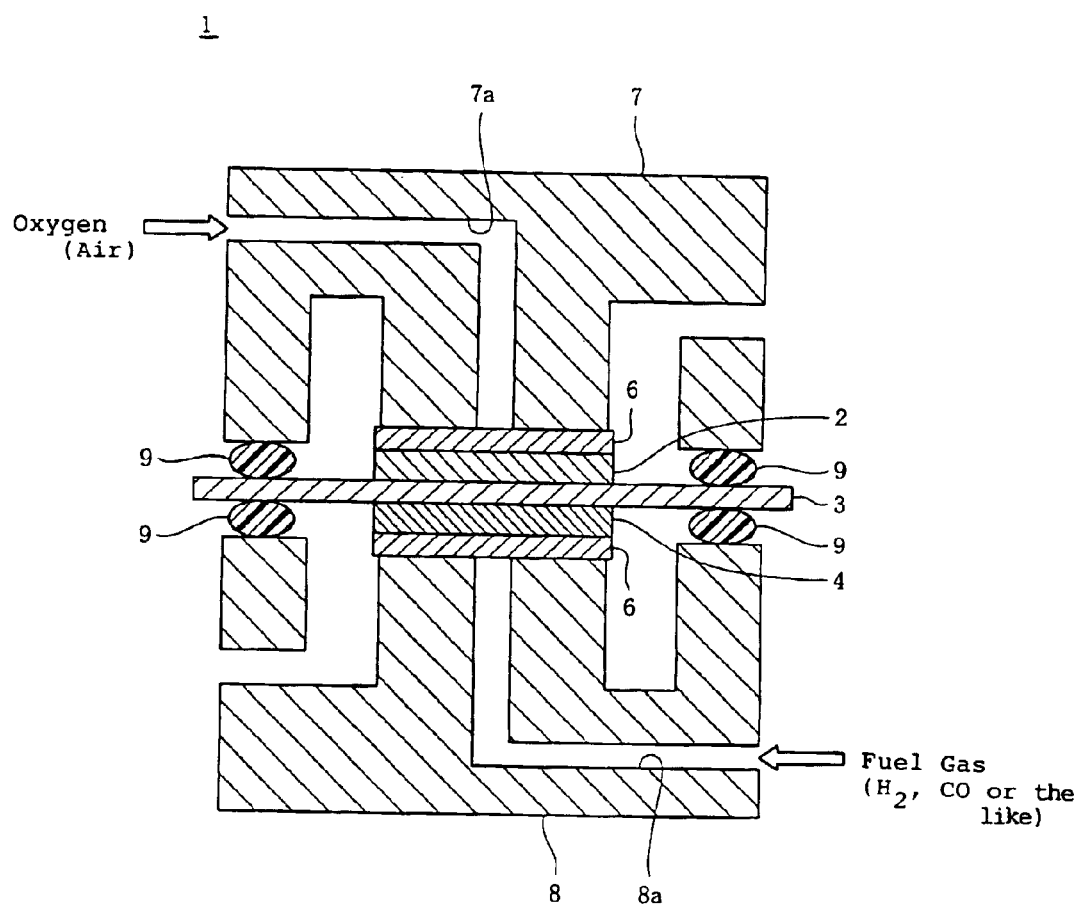
FIG. 5 is a schematic view showing a structure of a solid oxide fuel cell using an oxide ion conductor of the present invention as a solid electrolyte.

That is, since the oxide ion conductor of the present invention has oxide ionic conduction significantly superior to that of a conventional stabilized zirconia, for example, in the case in which a solid oxide fuel cell is formed by using an electrolyte composed of a thick film 0.5 mm (equal to 500 μm) thick which can be formed by a sintering method, a higher output can be obtained by using the oxide ion conductor of the present invention than that obtained by using the stabilized zirconia described above. In FIG. 5, a typical solid oxide fuel cell 1 is shown. The oxide ion conductor of the present invention is used as a solid electrolyte layer 3, and the solid electrolyte layer 3 is provided between an air electrode layer 2 and a fuel electrode layer 4 so as to form a planar type single cell. This single cell is held between a separator 7 at the air electrode side and a separator 8 at the fuel electrode side, each separator is coated with current collectors 6 and 6, respectively, by using washers 9 and 9. In this solid oxide fuel cell 1, power generation is performed by supplying oxygen (air) to the air electrode layer 2 via a supply opening 7a provided in the separator 7 at the air electrode side and by supplying a fuel gas ($H_2$, CO, or the like) to the fuel electrode layer 4 via a supply opening 8a provided in the separator 8 at the fuel electrode side. The oxygen supplied to the air electrode layer 2 reaches the vicinity of the interface with the solid electrolyte layer 3 via pores in the air electrode layer 2 and receives electrons from the air electrode layer 2 at this interface, whereby the oxygen is ionized to form oxide ions ($O^{2-}$). The oxide ions permeate the solid electrolyte layer 3 toward the fuel electrode layer 4. The oxide ions, which reach the vicinity of the interface with the fuel electrode layer 4, react with the fuel gas at the interface and generate a reaction product ($H_2O$, $CO_2$, or the like), whereby electrons are discharged to the fuel electrode. By collecting the electrons using the current collectors 6 and 6, current can be obtained.

Accordingly, the solid electrolyte layer 3 is a permeation media for the oxide ions, and even though depending on type of element B2 and the atomic ratio thereof, the maximum output density of the solid oxide fuel cell 1 using the oxide ion conductor of the present invention as the oxide electrolyte layer 3 exceeds that of a solid oxide fuel cell using a thin film 30 μm thick composed of a stabilized zirconia at an operating temperature of 1,000° C. and is several times (for example, 3 times or more) larger than that at an operating temperature of 800° C. In addition, when a film approximately 200 μm thick is used, an output density can be obtained at a lower temperature, such as 600 or 700° C., which is equivalent to that obtained at 1,000° C. by using a stabilized zirconia film 30 μm thick.

When the oxide ion conductor of the present invention is used as an electrolyte for a solid oxide fuel cell, materials to be used may be selected in accordance with an operating temperature. For example, in the case in which turbine generation using exhaust gases is performed as cogeneration, since a high operating temperature is required, such as approximately 1,000° C., it is preferable that an electrolyte be composed of the oxide ion conductor containing Co or Fe as the element B2, which exhibits high oxide ionic conduction at a higher temperature, and more preferably, the oxide ion conductor containing Co is used. On the other hand, when an operating temperature is approximately 800° C., in addition to the oxide ion conductor mentioned above, the oxide ion conductor containing Ni as the element B2 may be used, and when an operating temperature is 600° C. or less, the oxide ion conductor containing Cu as the element B2 may be used.

In the case in which an operating temperature is low, such as 600 to 700° C., when generation is simultaneously performed by using steam or other exhaust gases, or the energy thereof is effectively used as a heat source, the generation efficiency of the solid oxide fuel cell is not seriously decreased. When an operating temperature is lower as described above, since a steel material such as a stainless steel can be used as a structural material for the solid oxide fuel cell, there is an advantage in that the material cost can be significantly decreased compared to a material, such as a Ni—Cr alloy, or a ceramic, which must be used when an operating temperature is approximately 1,000° C. A solid oxide fuel cell functional at a lower temperature as described above cannot be constructed by using a conventional stabilized zirconia; however, according to the present invention, a solid oxide fuel cell can be constructed which is functional at from a lower to a higher operating temperature in accordance with the condition to be used.

Since the oxide ion conductor of the present invention exhibits high oxide ionic conduction in a wide range of temperature, the oxide ion conductor can be satisfactory used as an electrolyte for a solid oxide fuel cell which is operated at a relatively lower temperature, such as 600 to 700° C. and at a high temperature, such as approximately 1,000° C. As a result, when the oxide ion conductor is selected as an electrolyte, various solid oxide fuel cells from a low temperature-operating type to a high temperature-operating type can be constructed only by using this oxide ion conductor.

The largest application of a stabilized zirconia is currently in oxygen sensors, and a large number of the sensors are used for air-fuel control for automobiles and are also used for controlling industrial processes for steel manufacturing and the like. The oxygen sensor described above is called a solid electrolyte oxygen sensor and is used for measuring an oxygen concentration based on the principle of an oxygen concentration cell. That is, when an oxygen partial pressure at one end of a material composed of an oxide ion conductor differs from that at the other end of the material, oxide ions permeate the material to form a oxygen concentration cell;

hence, the oxygen partial pressure can be detected by measuring the electromotive force by providing electrodes at the both ends. The solid electrolyte oxygen sensor can also be used for gases containing oxygen, such as $SO_x$ and $NO_x$, in addition to an oxygen gas.

The oxygen sensors formed of a stabilized zirconia are relatively inexpensive; however, since the oxide ionic conduction is decreased at a lower temperature and can only be used at a higher temperature of 600° C. or more, the applications thereof are restricted. In contrast, since the oxide ion conductor of the present invention, in which the oxide ionic conduction is dominant, exhibits higher oxide ionic conduction compared to that of a stabilized zirconia, they can be effectively used for gas sensors, and particularly, for oxygen sensors, and in addition, since the oxide ionic conduction is high even at a lower temperature, a gas sensor formed of the oxide ion conductor of the present invention can be satisfactory used at 600° C. or less.

In addition, the oxide ion conductor of the present invention, in which the oxide ionic conduction is dominant, can also be used as an oxygen separation membrane for an electrochemical oxygen pump. When a potential difference is applied between two ends of a separation membrane composed of an oxide ion conductor, the oxide ions permeate the membrane, and current flows, whereby oxygen flows in one direction from one end to the other end of the membrane. This is the oxygen pump. For example, when air is supplied from one end of the membrane, oxygen-enriched air can be obtained at the other end of the membrane, whereby the oxide ion conductor is used as an oxygen separation membrane. The oxygen separation membranes described above are used in, for example, military aircraft or helicopters for producing oxygen-enriched air form the thin air of the surrounding area. It is also believed that the oxide separation membrane may be used instead of oxygen cylinders for medical use.

The gas separation membrane described above can also be used for, for example, decomposition of water and $NO_x$, in addition to oxygen separation. In the case in which water is decomposed on the surface of a separation membrane into oxide ions and hydrogen, since a difference of oxide ion concentration is generated between the two ends of the membrane, the flow of the oxide ions is produced by a driving force of the difference described above, and the hydrogen does not flow but remains, whereby hydrogen can be produced from water. In the case in which $NO_x$ is decomposed, the $NO_x$ is turned into harmless substances and is decomposed into nitrogen and oxygen.

In addition, the oxide ion conductor of the present invention may be used for electrochemical reactors or separation membranes for isotopic oxygen.

EXAMPLES

Next, the examples of the present invention will be described in detail together with the comparative examples.

Examples 1 to 7

A basic powdered mixture (hereinafter referred to as "LSGMC") was prepared which was composed of powdered metal oxides, $La_2O_3$, $La_2SrCO_3$, $Ga_2O_3$, MgO, and CoO, in accordance with ratios so as to form $La_{0.8}Sr_{0.2}Ga_{0.8}Mg_{0.15}Co_{0.05}O_3$.

After a powdered material composed of $Al_2O_3$ was mixed with the powdered mixture in a ratio in accordance with that shown in Table 1, toluene and n-butanol were added thereto as a solvent so as to impart fluidity to the mixture, and a film having a thickness of 0.25 to 0.30 mm was then formed by a doctor blade method. Subsequently, the film thus formed was sintered at 1,450° C. for 6 hours, thereby yielding an oxide ion conductor. Oxide ion conductors formed in a manner described above were used for Examples 1 to 7.

Examples 8 to 15

A powdered mixture was prepared which was composed of the same LSGMC as that prepared in Example 1. After a powdered material composed of MgO was mixed with the powdered mixture described above in a ratio in accordance with that shown in Table 1, the same solvent as that used in Example 1 was added, a film was then formed having the same thickness as that in Example 1 by a doctor blade method, and an oxide ion conductor was obtained by sintering under the same condition as that in Example 1. Oxide ion conductors formed in a manner described above were used for Example 8 to 15.

Examples 16 to 22

A powdered mixture was prepared which was composed of the same LSGMC as that prepared in Example 1. After a powdered material composed of $ZrO_2$ was mixed with the powdered mixture described above in a ratio in accordance with that shown in Table 1, the same solvent as that used in Example 1 was added, a film was then formed having the same thickness as that in Example 1 by a doctor blade method, and an oxide ion conductor was obtained by sintering under the same condition as that in Example 1. Oxide ion conductors formed in a manner described above were used for Example 16 to 22.

Examples 23 to 26

A powdered mixture was prepared which was composed of the same LSGMC as that prepared in Example 1. After a powdered material composed of $Al_2O_3$ and MgO is mixed with the powdered mixture described above in a ratio in accordance with that shown in Table 2, the same solvent as that used in Example 1 is added, a film is then formed having the same thickness as that in Example 1 by a doctor blade method, and an oxide ion conductor is obtained by sintering under the same condition as that in Example 1. Oxide ion conductors formed in a manner described above are used for Example 23 to 26.

Examples 27 to 30

A powdered mixture was prepared which was composed of the same LSGMC as that prepared in Example 1. After a powdered material composed of $Al_2O_3$ and $ZrO_2$ is mixed with the powdered mixture described above in a ratio in accordance with that shown in Table 2, the same solvent as that used in Example 1 is added, a film is then formed having the same thickness as that in Example 1 by a doctor blade method, and an oxide ion conductor is obtained by sintering under the same condition as that in Example 1. Oxide ion conductors formed in a manner described above are used for Example 27 to 30.

Examples 31 to 34

A powdered mixture was prepared which was composed of the same LSGMC as that prepared in Example 1. After a powdered material composed of MgO and $ZrO_2$ is mixed with the powdered mixture described above in a ratio in accordance with that shown in Table 2, the same solvent as that used in Example 1 is added, a film is then formed having the same thickness as that in Example 1 by a doctor blade method, and an oxide ion conductor is obtained by sintering under the same condition as that in Example 1. Oxide ion conductors formed in a manner described above are used for Example 31 to 34.

Examples 35 to 39

A powdered mixture was prepared which was composed of the same LSGMC as that prepared in Example 1. After a powdered material composed of $Al_2O_3$, MgO, and $ZrO_2$ is mixed with the powdered mixture described above in a ratio in accordance with that shown in Table 2, the same solvent as that used in Example 1 is added, a film is then formed having the same thickness as that in Example 1 by a doctor blade method, and an oxide ion conductor is obtained by sintering under the same condition as that in Example 1. Oxide ion conductors formed in a manner described above are used for Example 35 to 39.

Examples 40 to 46

A powdered mixture was prepared which was composed of the same LSGMC as that prepared in Example 1. After a powdered material composed of CoO is mixed with the powdered mixture described above in a ratio in accordance with that shown in Table 3, the same solvent as that used in Example 1 is added, a film is then formed having the same thickness as that in Example 1 by a doctor blade method, and an oxide ion conductor is obtained by sintering under the same condition as that in Example 1. Oxide ion conductors formed in a manner described above are used for Example 40 to 46.

Examples 47 to 53

A powdered mixture was prepared which was composed of the same LSGMC as that prepared in Example 1. After a powdered material composed of $Fe_2O_3$ is mixed with the powdered mixture described above in a ratio in accordance with that shown in Table 3, the same solvent as that used in Example 1 is added, a film is then formed having the same thickness as that in Example 1 by a doctor blade method, and an oxide ion conductor is obtained by sintering under the same condition as that in Example 1. Oxide ion conductors formed in a manner described above are used for Example 47 to 53.

Examples 54 to 60

A powdered mixture was prepared which was composed of the same LSGMC as that prepared in Example 1. After a powdered material composed of NiO is mixed with the powdered mixture described above in a ratio in accordance with that shown in Table 3, the same solvent as that used in Example 1 is added, a film is then formed having the same thickness as that in Example 1 by a doctor blade method, and an oxide ion conductor is obtained by sintering under the same condition as that in Example 1. Oxide ion conductors formed in a manner described above are used for Example 54 to 60.

Examples 61 to 67

A powdered mixture was prepared which was composed of the same LSGMC as that prepared in Example 1. After a powdered material composed of CuO is mixed with the powdered mixture in a ratio in accordance with that shown in Table 4, the same solvent as that used in Example 1 is added, a film is then formed having the same thickness as that in Example 1 by a doctor blade method, and an oxide ion conductor is obtained by sintering under the same condition as that in Example 1. Oxide ion conductors formed in a manner as described above are used for Example 61 to 67.

Examples 68 to 74

A powdered mixture was prepared which was composed of the same LSGMC as that prepared in Example 1. After a powdered material composed of ZnO is mixed with the powdered mixture described above in a ratio in accordance with that shown in Table 4, the same solvent as that used in Example 1 is added, a film is then formed having the same thickness as that in Example 1 by a doctor blade method, and an oxide ion conductor is obtained by sintering under the same condition as that in Example 1. Oxide ion conductors formed in a manner described above are used for Example 68 to 74.

Examples 75 to 80

A powdered mixture was prepared which was composed of the same LSGMC as that prepared in Example 1. After a powdered material composed of MnO is mixed with the powdered mixture in a ratio in accordance with that shown in Table 4, the same solvent as that used in Example 1 is added, a film is then formed having the same thickness as that in Example 1 by a doctor blade method, and an oxide ion conductor is obtained by sintering under the same condition as that in Example 1. Oxide ion conductors formed in a manner described above are used for Example 75 to 80.

Comparative Examples 1

The same solvent as that used in Example 1 was added to the powdered mixture prepared in Example 1 having no additive therein, a film was then formed having the same thickness as that in Example 1 by a doctor blade method, and the film thus formed was sintered under the same condition as that in Example 1, whereby an oxide ion conductor was obtained which was used as the standard for comparison. This oxide ion conductor (non-doped LSGMC) was used for Comparative Example 1.

Comparative Examples 2 to 14

A powdered mixture was prepared which was composed of the same LSGMC as that prepared in Example 1. Powdered metal oxides composed of $Al_2O_3$, MgO, $ZrO_2$, CoO, $Fe_2O_3$, NiO, CuO, and MnO were selected as shown in Tables 1 and 4, and each selected powdered metal oxide was mixed with the powdered mixture described above in a ratio in accordance with that shown in Tables 1 to 4. Subsequently, the same solvent as that used in Example 1 was added, a film was then formed having the same thickness as that in Example 1 by a doctor blade method, and an oxide ion conductor was obtained by sintering under the same condition as that in Example 1. The oxide ion conductors formed in a manner described above were used for Comparative Example 2 to 14.

Comparative Evaluation

The oxide ion conductors thus formed were observed by a scanning electron microscope (SEM) and were analyzed by an electron probe micro analyzer (EPMA), and in addition, the resistivities of the oxide ion conductors at 650 and 800° C. and the mechanical strengths thereof were measured. The measurement of the resistivity was conducted by steps of coating platinum paste to be used as electrodes on each sample thus prepared, connecting platinum wires and baking at 950 to 1,200° C. for 10 to 60 minutes, and measuring the resistivities by a DC four-point probe method or by an AC two-point probe method in a chamber in which a oxygen partial pressure and a temperature were optionally controlled. An oxygen partial pressure was controlled by using mixed gases, i.e., $O_2$—$N_2$, CO—$CO_2$, and $H_2$—$H_2O$.

Concerning the measurement of the mechanical strength, a test piece 4 mm by 4 mm by 0.23 mm was cut away from the sample thus formed, and a three-point bending test was performed by using the test piece. The results are shown in Tables 1 to 4.

Figure 2:
FIG. 2 is a SEM photograph of an oxide ion conductor of Example 12, which is composed of LSGMC mixed with 3.6 percent by weight of MgO.
Figure 3:
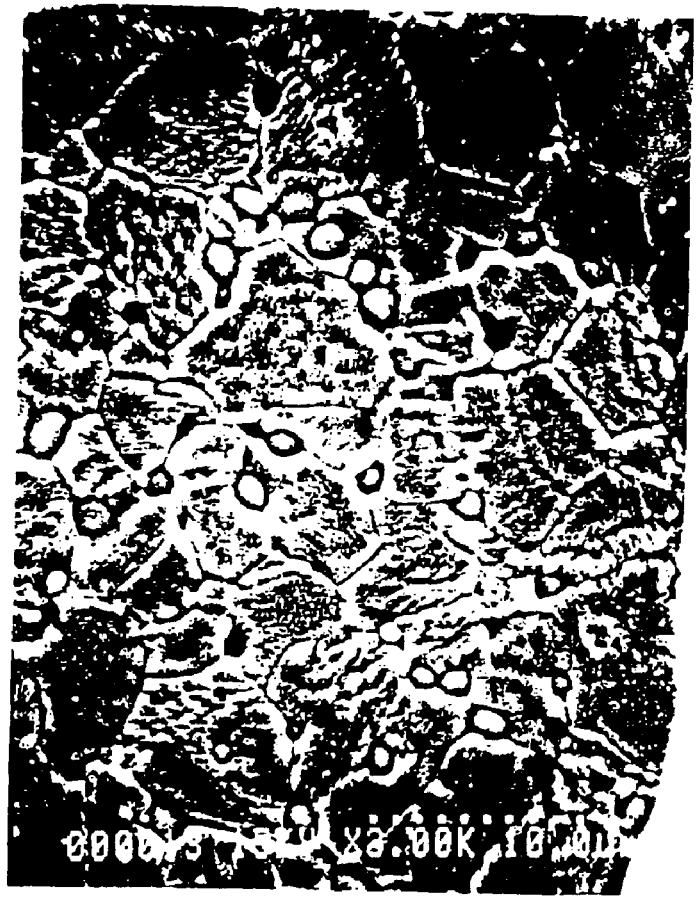
FIG. 3 is a SEM photograph of an oxide ion conductor of Example 19, which is composed of LSGMC mixed with 2 percent by weight of ZrO$_2$.
Figure 4:
FIG. 4 is a SEM photograph of an oxide ion conductor of Comparative Example 1, which is composed of LSGMC mixed with no additive.

The results of EPMA analysis, resistivities, and mechanical strengths obtained for Examples 1 to 80 and for Comparative Examples 1 to 14 are shown in Tables 1 to 4. In addition, the SEM photographs of the oxide ion conductors of Examples 4, 12, and 19 are shown in FIGS. 1 to 3, in that order, and the SEM photograph of the oxide ion conductor of Comparative Example 1 used as the standard is shown in FIG. 4.

TABLE 1

|  | Manufacturing method | Content of element (wt %) | | | | | | Resistivity ($\Omega$ cm) at 650° C. | Resistivity ($\Omega$ cm) at 800° C. | Strength (kgf/mm$^2$) at R.T. |
| --- | --- | --- | --- | --- | --- | --- | --- | --- | --- | --- |
|  |  | La | Sr | Ga | Mg | Co | Al/Zr |  |  |  |
| Comparative Example 1 | Non-dope LSGMC | 47.12 | 7.43 | 23.65 | 1.55 | 1.25 | 0.00 | 19.23 | 5.99 | 19.98 |
| Example 1 | Al$_2$O$_3$-0.05 wt % LSGMC | 47.52 | 7.26 | 23.26 | 1.52 | 1.20 | 0.23 | 19.52 | 6.32 | 21.54 |
| Example 2 | Al$_2$O$_3$-0.2 wt % LSGMC | 47.60 | 7.23 | 23.21 | 1.51 | 1.15 | 0.29 | 20.64 | 7.86 | 24.79 |
| Example 3 | Al$_2$O$_3$-1 wt % LSGMC | 48.74 | 6.52 | 22.51 | 1.50 | 1.15 | 0.57 | 22.32 | 8.6 | 26.03 |
| Example 4 | Al$_2$O$_3$-2 wt % LSGMC | 49.93 | 5.67 | 21.54 | 1.50 | 1.16 | 1.14 | 41.52 | 13.52 | 29.08 |
| Example 5 | Al$_2$O$_3$-3 wt % LSGMC | 50.64 | 5.55 | 50.91 | 1.48 | 1.11 | 1.30 | 58.71 | 18.53 | 26.05 |
| Example 6 | Al$_2$O$_3$-4 wt % LSGMC | 50.93 | 5.49 | 20.47 | 1.48 | 1.09 | 1.52 | 76.51 | 24.32 | 25.32 |
| Example 7 | Al$_2$O$_3$-5 wt % LSGMC | 51.14 | 5.47 | 20.09 | 1.49 | 1.09 | 1.70 | 95.48 | 31.59 | 24.65 |
| Comparative Example 2 | Al$_2$O$_3$-6 wt % LSGMC | 51.48 | 5.29 | 19.86 | 1.47 | 1.04 | 1.84 | 114.95 | 37.84 | 23.47 |
| Example 8 | MgO-0.05 wt % LSGMC | 47.32 | 7.28 | 23.64 | 1.57 | 1.20 | 0.00 | 20.37 | 6.27 | 20.85 |
| Example 9 | MgO-0.2 wt % LSGMC | 47.44 | 7.20 | 23.63 | 1.60 | 1.12 | 0.00 | 20.78 | 6.99 | 21.76 |
| Example 10 | MgO-1 wt % LSGMC | 47.11 | 7.57 | 23.50 | 1.70 | 1.10 | 0.00 | 21.51 | 7.18 | 23.19 |
| Example 11 | MgO-1.8 wt % LSGMC | 46.82 | 8.04 | 23.35 | 1.94 | 1.09 | 0.00 | 22.94 | 7.27 | 25.74 |
| Example 12 | MgO-3.6 wt % LSGMC | 46.20 | 8.75 | 22.71 | 2.14 | 1.10 | 0.00 | 25.04 | 7.96 | 27.47 |
| Example 13 | MgO-5.4 wt % LSGMC | 45.45 | 9.40 | 22.75 | 2.19 | 1.08 | 0.00 | 30.6 | 9.67 | 24.47 |
| Example 14 | MgO-10 wt % LSGMC | 45.39 | 9.60 | 22.48 | 2.34 | 1.03 | 0.00 | 62.34 | 20.96 | 23.75 |
| Example 15 | MgO-15 wt % LSGMC | 45.05 | 10.14 | 22.03 | 2.62 | 0.96 | 0.00 | 94.65 | 33.12 | 22.69 |
| Comparative Example 3 | MgO-16 wt % LSGMC | 44.98 | 10.33 | 21.81 | 2.77 | 0.89 | 0.00 | 116.97 | 37.49 | 20.97 |
| Example 16 | ZrO$_2$-0.05 wt % LSGMC | 47.24 | 7.40 | 23.51 | 1.56 | 1.20 | 0.27 | 19.97 | 6.73 | 23.51 |
| Example 17 | ZrO$_2$-0.2 wt % LSGMC | 47.95 | 6.91 | 23.24 | 1.56 | 1.15 | 0.66 | 23.55 | 7.64 | 24.86 |
| Example 18 | ZrO$_2$-1 wt % LSGMC | 48.29 | 6.73 | 23.05 | 1.57 | 1.03 | 1.08 | 26.43 | 7.99 | 31.42 |
| Example 19 | ZrO$_2$-2 wt % LSGMC | 48.59 | 6.64 | 22.70 | 1.58 | 0.98 | 1.67 | 32.88 | 9.79 | 32.12 |
| Example 20 | ZrO$_2$-3 wt % LSGMC | 48.93 | 6.50 | 22.33 | 1.60 | 0.96 | 2.22 | 50.73 | 16.42 | 33.37 |
| Example 21 | ZrO$_2$-4 wt % LSGMC | 49.15 | 6.39 | 22.20 | 1.61 | 0.88 | 2.49 | 66.75 | 23.19 | 34.29 |
| Example 22 | ZrO$_2$-5 wt % LSGMC | 49.42 | 6.29 | 21.88 | 1.59 | 0.86 | 3.08 | 84.67 | 28.46 | 35.96 |
| Comparative Example 4 | ZrO$_2$-6 wt % LSGMC | 49.60 | 6.18 | 21.83 | 1.56 | 0.78 | 3.39 | 104.32 | 35.19 | 37.42 |

TABLE 2

|  | Manufacturing method | Content of element (wt %) | | | | | | Resistivity ($\Omega$ cm) at 650° C. | Resistivity ($\Omega$ cm) at 800° C. | Strength (kgf/mm$^2$) at R.T. |
| --- | --- | --- | --- | --- | --- | --- | --- | --- | --- | --- |
|  |  | La | Sr | Ga | Mg | Co | Al/Zr |  |  |  |
| Example 23 | Al$_2$O$_3$.MgO-0.05 wt % LSGMC | 47.17 | 7.63 | 23.14 | 1.60 | 1.21 | 0.23 | 19.99 | 6.54 | 21.89 |
| Example 24 | Al$_2$O$_3$.MgO-0.2 wt % LSGMC | 47.16 | 7.91 | 22.77 | 1.64 | 1.19 | 0.39 | 20.78 | 7.37 | 22.87 |
| Example 25 | Al$_2$O$_3$.MgO-1 wt % LSGMC | 46.97 | 8.07 | 22.59 | 1.68 | 1.17 | 0.46 | 35.61 | 7.55 | 25.34 |
| Example 26 | Al$_2$O$_3$.MgO-3 wt % LSGMC | 46.77 | 8.47 | 22.14 | 1.76 | 1.10 | 0.67 | 67.29 | 11.57 | 26.41 |
| Comparative Example 5 | Al$_2$O$_3$.MgO-5 wt % LSGMC | 46.58 | 8.83 | 21.74 | 1.89 | 1.05 | 0.78 | 101.02 | 20.64 | 24.19 |
| Example 27 | Al$_2$O$_3$.ZrO$_2$-0.05 wt % LSGMC | 47.58 | 7.36 | 22.90 | 1.52 | 1.21 | 0.88 | 19.78 | 6.49 | 23.74 |
| Example 28 | Al$_2$O$_3$.ZrO$_2$-0.2 wt % LSGMC | 48.04 | 7.02 | 22.78 | 1.50 | 1.18 | 1.03 | 21.74 | 7.53 | 24.99 |
| Example 29 | Al$_2$O$_3$.ZrO$_2$-1 wt % LSGMC | 48.34 | 6.88 | 22.54 | 1.49 | 1.13 | 1.34 | 24.76 | 8.23 | 28.71 |
| Example 30 | Al$_2$O$_3$.ZrO$_2$-3 wt % LSGMC | 48.67 | 6.65 | 22.41 | 1.47 | 1.08 | 1.54 | 54.19 | 17.09 | 30.19 |
| Comparative Example 6 | Al$_2$O$_3$.ZrO$_2$-5 wt % LSGMC | 51.72 | 6.51 | 22.13 | 1.45 | 0.98 | 1.97 | 102.64 | 20.94 | 30.91 |
| Example 31 | MgO.ZrO$_2$-0.05 wt % LSGMC | 47.05 | 7.61 | 23.44 | 1.56 | 1.20 | 0.43 | 20.19 | 6.71 | 22.09 |
| Example 32 | MgO.ZrO$_2$-0.2 wt % LSGMC | 46.41 | 8.26 | 23.30 | 1.60 | 1.14 | 0.82 | 20.68 | 7.43 | 23.43 |
| Example 33 | MgO.ZrO$_2$-1 wt % LSGMC | 46.18 | 8.55 | 23.15 | 1.64 | 1.06 | 1.14 | 26.89 | 7.61 | 25.71 |
| Example 34 | MgO.ZrO$_2$-3 wt % LSGMC | 45.96 | 8.86 | 22.95 | 4.69 | 1.02 | 1.46 | 49.37 | 10.69 | 28.69 |
| Comparative Example 7 | MgO.ZrO$_2$-5 wt % LSGMC | 42.91 | 9.04 | 22.73 | 1.73 | 0.97 | 1.82 | 100.03 | 19.64 | 30.03 |
| Example 35 | Al$_2$O$_3$.MgO.ZrO$_2$-0.05 wt % LSGMC | 47.18 | 7.72 | 22.88 | 1.58 | 1.24 | 0.81 | 20.31 | 6.19 | 20.94 |
| Example 36 | Al$_2$O$_3$.MgO.ZrO$_2$-0.2 wt % LSGMC | 46.61 | 8.34 | 22.65 | 1.60 | 1.19 | 1.17 | 21.48 | 7.04 | 24.69 |
| Example 37 | Al$_2$O$_3$.MgO.ZrO$_2$-1 wt % LSGMC | 46.09 | 8.88 | 22.56 | 1.63 | 1.10 | 1.41 | 22.09 | 8.31 | 25.55 |
| Example 38 | Al$_2$O$_3$.MgO.ZrO$_2$-3 wt % LSGMC | 45.65 | 9.39 | 22.31 | 1.67 | 1.05 | 1.73 | 46.97 | 13.49 | 29.17 |
| Example 39 | Al$_2$O$_3$.MgO.ZrO$_2$-5 wt % LSGMC | 44.69 | 10.27 | 22.31 | 1.71 | 0.98 | 1.89 | 73.49 | 22.19 | 30.19 |
| Comparative Example 8 | Al$_2$O$_3$.MgO.ZrO$_2$-7 wt % LSGMC | 43.79 | 11.23 | 21.95 | 1.77 | 0.97 | 2.33 | 119.49 | 34.76 | 32.45 |

TABLE 3

| | | Content of element (wt %) | | | | | Resistivity (Ω cm) at 650° C. | Resistivity (Ω cm) at 800° C. | Strength (kgf/mm²) at R.T. |
|---|---|---|---|---|---|---|---|---|---|
| | | La | Sr | Ga | Mg | Co | Fe/Ni/Cu/Zn/Mn | | |
| Example 40 | CoO-0.05 wt % LSGMC | 45.691 | 8.609 | 23.798 | 1.537 | 1.334 | 0.000 | 19.23 | 6.43 | 20.94 |
| Example 41 | CoO-0.2 wt % LSGMC | 45.157 | 9.045 | 23.861 | 1.530 | 1.363 | 0.000 | 21.89 | 7.77 | 23.76 |
| Example 42 | CoO-1 wt % LSGMC | 44.508 | 9.559 | 23.898 | 1.493 | 1.493 | 0.000 | 24.1 | 8.57 | 25.19 |
| Example 43 | CoO-2 wt % LSGMC | 44.250 | 9.756 | 23.889 | 1.463 | 1.596 | 0.000 | 41.97 | 12.94 | 27.16 |
| Example 44 | CoO-3 wt % LSGMC | 44.063 | 9.919 | 23.798 | 1.454 | 1.725 | 0.000 | 60.12 | 19.16 | 27.94 |
| Example 45 | CoO-4 wt % LSGMC | 43.781 | 10.111 | 23.867 | 1.402 | 1.802 | 0.000 | 77.19 | 23.87 | 29.1 |
| Example 46 | CoO-5 wt % LSGMC | 43.648 | 10.183 | 23.830 | 1.339 | 1.979 | 0.000 | 96.43 | 30.94 | 27.16 |
| Comparative Example 9 | CoO-6 wt % LSGMC | 43.469 | 10.297 | 23.830 | 1.287 | 2.106 | 0.000 | 120.69 | 38.49 | 26.17 |
| Example 47 | Fe₂O₃-0.05 wt % LSGMC | 47.099 | 7.567 | 23.404 | 1.530 | 1.229 | 0.333 | 18.69 | 6.48 | 21.64 |
| Example 48 | Fe₂O₃-0.2 wt % LSGMC | 49.045 | 7.652 | 23.347 | 1.491 | 1.180 | 0.547 | 19.46 | 7.88 | 23.79 |
| Example 49 | Fe₂O₃-1 wt % LSGMC | 49.177 | 5.909 | 23.038 | 1.465 | 1.143 | 0.635 | 22.16 | 8.57 | 25.94 |
| Example 50 | Fe₂O₃-2 wt % LSGMC | 46.364 | 8.249 | 23.391 | 1.456 | 1.135 | 0.741 | 40.19 | 13.57 | 29.01 |
| Example 51 | Fe₂O₃-3 wt % LSGMC | 16.025 | 8.526 | 23.461 | 1.438 | 1.111 | 0.790 | 57.46 | 18.64 | 27.13 |
| Example 52 | Fe₂O₃-4 wt % LSGMC | 45.834 | 8.685 | 23.515 | 1.408 | 1.062 | 0.887 | 77.16 | 23.94 | 26.43 |
| Example 53 | Fe₂O₃-5 wt % LSGMC | 45.499 | 8.964 | 23.587 | 1.379 | 1.013 | 0.984 | 94.61 | 30.84 | 25.13 |
| Comparative Example 10 | Fe₂O₃-6 wt % LSGMC | 43.442 | 9.168 | 23.598 | 1.361 | 0.964 | 1.106 | 110.67 | 36.19 | 24.36 |
| Example 54 | NiO-0.05 wt % LSGMC | 46.675 | 7.968 | 23.339 | 1.515 | 1.233 | 0.526 | 19.44 | 6.55 | 20.49 |
| Example 55 | NiO-0.2 wt % LSGMC | 46.257 | 8.423 | 23.159 | 1.512 | 1.214 | 0.831 | 21.06 | 7.61 | 23.14 |
| Example 56 | NiO-1 wt % LSGMC | 45.703 | 8.905 | 23.211 | 1.497 | 1.167 | 0.961 | 22.73 | 8.48 | 25.37 |
| Example 57 | NiO-2 wt % LSGMC | 45.173 | 9.347 | 23.307 | 1.480 | 1.120 | 1.039 | 40.59 | 13.4 | 28.33 |
| Example 58 | NiO-3 wt % LSGMC | 44.610 | 9.842 | 23.284 | 1.455 | 1.073 | 1.273 | 57.49 | 18.29 | 27.11 |
| Example 59 | NiO-4 wt % LSGMC | 44.221 | 10.213 | 23.319 | 1.438 | 1.025 | 1.404 | 75.49 | 25.64 | 26.34 |
| Example 60 | NiO-5 wt % LSGMC | 43.280 | 11.043 | 23.341 | 1.425 | 1.006 | 1.592 | 93.87 | 31.59 | 25.09 |
| Comparative Example 11 | NiO-6 wt % LSGMC | 42.653 | 11.586 | 23.400 | 1.388 | 0.958 | 1.779 | 112.49 | 36.49 | 23.16 |

TABLE 4

| | | Content of element (wt %) | | | | | Resistivity (Ω cm) at 650° C. | Resistivity (Ω cm) at 800° C. | Strength (kgf/mm²) at R.T. |
|---|---|---|---|---|---|---|---|---|---|
| | | La | Sr | Ga | Mg | Co | Fe/Ni/Cu/Zn/Mn | | |
| Example 61 | CuO-0.05 wt % LSGMC | 46.758 | 7.888 | 23.351 | 1.493 | 1.232 | 0.596 | 18.49 | 7.16 | 21.46 |
| Example 62 | CuO-0.2 wt % LSGMC | 46.567 | 8.093 | 23.284 | 1.476 | 1.210 | 0.788 | 21.78 | 7.94 | 23.11 |
| Example 63 | CuO-1 wt % LSGMC | 46.339 | 8.293 | 23.320 | 1.447 | 1.161 | 0.925 | 24.51 | 8.74 | 25.87 |
| Example 64 | CuO-2 wt % LSGMC | 46.080 | 8.487 | 23.428 | 1.385 | 1.111 | 1.062 | 40.2 | 13.49 | 28.13 |
| Example 65 | CuO-3 wt % LSGMC | 45.906 | 8.601 | 23.551 | 1.334 | 1.061 | 1.144 | 60.43 | 18.46 | 27.61 |
| Example 66 | CuO-4 wt % LSGMC | 45.678 | 8.802 | 23.586 | 1.304 | 1.012 | 1.282 | 77.19 | 25.19 | 26 |
| Example 67 | CuO-5 wt % LSGMC | 45.467 | 8.958 | 23.661 | 1.211 | 0.987 | 1.501 | 97.84 | 32.17 | 25.16 |
| Comparative Example 12 | CuO-6 wt % LSGMC | 45.216 | 9.156 | 23.745 | 1.150 | 0.938 | 1.667 | 109.49 | 37.94 | 24.31 |
| Example 68 | ZnO-0.05 wt % LSGMC | 47.523 | 7.401 | 22.902 | 1.545 | 1.257 | 0.865 | 19.99 | 6.51 | 21.06 |
| Example 69 | ZnO-0.2 wt % LSGMC | 47.714 | 7.244 | 22.910 | 1.523 | 1.206 | 0.947 | 21.69 | 8.06 | 23.87 |
| Example 70 | ZnO-1 wt % LSGMC | 48.042 | 7.016 | 22.838 | 1.511 | 1.104 | 1.142 | 24.1 | 8.74 | 25.64 |
| Example 71 | ZnO-2 wt % LSGMC | 48.732 | 6.475 | 22.713 | 1.487 | 1.051 | 1.305 | 40.97 | 13.64 | 29.13 |
| Example 72 | ZnO-3 wt % LSGMC | 48.897 | 6.362 | 22.708 | 1.466 | 0.951 | 1.472 | 57.34 | 19.16 | 27.03 |
| Example 73 | ZnO-4 wt % LSGMC | 48.970 | 6.282 | 22.776 | 1.423 | 0.900 | 1.553 | 77.18 | 24.31 | 26.13 |
| Example 74 | ZnO-5 wt % LSGMC | 49.110 | 6.166 | 22.788 | 1.381 | 0.849 | 1.691 | 94.31 | 31.49 | 25.64 |
| Comparative Example 13 | ZnO-6 wt % LSGMC | 49.685 | 5.705 | 22.728 | 1.336 | 0.772 | 1.880 | 117.49 | 36.19 | 24.73 |
| Example 75 | MnO-0.05 wt % LSGMC | 46.949 | 7.636 | 23.566 | 1.509 | 1.203 | 0.257 | 18.97 | 5.98 | 20.94 |
| Example 76 | MnO-0.2 wt % LSGMC | 46.838 | 7.806 | 23.451 | 1.482 | 1.131 | 0.539 | 21 | 7.67 | 23.43 |
| Example 77 | MnO-1 wt % LSGMC | 46.551 | 8.090 | 23.396 | 1.455 | 1.108 | 0.728 | 22.74 | 8.4 | 25.7 |
| Example 78 | MnO-2 wt % LSGMC | 46.354 | 8.295 | 23.357 | 1.437 | 1.060 | 0.894 | 42.16 | 13.64 | 28.69 |
| Example 79 | MnO-3 wt % LSGMC | 46.064 | 8.533 | 23.451 | 1.397 | 0.986 | 1.013 | 57.34 | 18.7 | 27.08 |
| Example 80 | MnO-4 wt % LSGMC | 45.869 | 8.691 | 23.533 | 1.346 | 0.911 | 1.156 | 75.73 | 25.19 | 26.31 |
| Comparative Example 14 | MnO-5 wt % LSGMC | 45.518 | 8.968 | 23.657 | 1.286 | 0.836 | 1.299 | 105.68 | 30.98 | 25.99 |

Evaluation

As can been seen from Tables 1 to 4, the mechanical strengths of the oxide ion conductors of Examples 1 to 80 were better than that of Comparative Example 1 which contains no metal element B3. In addition, it was also confirmed that the resistivities at a low temperature of 650° C. of the oxide ion conductors of Comparative Examples 2 to 14, which were out of the ranges of the present invention, were increased to a level approximately equivalent to that of 8-YSZ (8 mol % $Y_2O_3$—$ZrO_2$) at 650° C. (approximately 120 Ω·cm), which was used as a conventional oxide ion conductor in practice, or the mechanical strengths were not satisfactory improved.

Furthermore, as shown in FIG. 4, it was confirmed that the matrix crystal grains of Comparative Example 1 composed of the LSGMC, which contained no metal element B3, were larger than those of Examples 4, 12, and 19, shown in FIGS. 1 to 3, and that the first and the second crystal grains were present between the matrix crystal grains shown in FIGS. 1 to 3. Hence, it is believed that the mechanical strengths of Examples 4, 12, and 19 were improved. It is also understood that the grain diameters of the first and the second crystal grains were 0.1 to 2.0 μm, and the volume fractions thereof were 0.5 to 20 percent by volume.

As thus has been described, according to the present invention, an oxide ion conductor can be obtained having oxide ionic conduction higher than that of a stabilized zirconia, which is a conventionally typical oxide ion conductor, and having a relatively higher mechanical strength. Accordingly, the oxide ion conductor of the present invention can be used at a lower temperature than a stabilized zirconia. In addition, since the oxide ion conductor of the present invention exhibits high oxide ionic conductance at all oxygen partial pressures from an oxygen atmosphere to a hydrogen atmosphere, the oxide ion conductor can be effectively used as electrolytes for solid oxide fuel cells, gas sensors, such as oxygen gas sensors, and oxygen separation membranes for electrochemical oxygen pumps, whereby products having performances superior to those of conventional products may be produced.

According to the oxide ion conductor of the present invention, the first crystal grains composed of elements Ln1, A, and Ga and the second crystal grains composed of element B are present between or in the matrix crystal grains other than the first and the second crystal grains, the grain diameters of the first and the second crystal grains are 0.1 to 2.0 μm, the volume fractions thereof are 0.5 to 20 percent by volume, and the grain diameter of the matrix crystal grains is 2.0 to 7.0 μm. Accordingly, the oxide ion conductor of the present invention has a relatively high mechanical strength, and in addition, the oxide ion conductor maintains higher oxide ionic conduction in a wide range of temperature and a wide range of oxygen partial pressure from an oxygen atmosphere to a substantial hydrogen atmosphere, whereby the oxide ion conductor of the present invention has significant advantages.

This application claims priority under 35 U.S.C. § 119 to Japanese patent applications JP 2000-71759 filed on Mar. 15, 2000 and JP 2000-213659 filed on Jul. 14, 2000, which are incorporated by references herein for its entirety.

What is claimed is:

1. An oxide ion conductor represented by the formula Ln1AGaB1B2B3O, wherein Ln1 is at least one element selected from the group consisting of La, Ce, Pr, Nd, and Sm, the content thereof being 43.6 to 51.2 percent by weight, A is at least one element selected from the group consisting of Sr, Ca, an Ba, the content thereof being 5.4 to 11.1 percent by weight, the content of Ga is 20.0 to 23.9 percent by weight, B1 is at least one element selected from the group consisting of Mg, Al, In, B2 is at least one element selected from the group consisting of Co, Fe, Ni, and Cu, B3 is at least one element selected from the group consisting Al, Mg, Co, Ni, Fe, Cu, Zn, Mn, and Zr, wherein, B3 is an element different from B1 and B2, the content of B1 is 1.21 to 1.76 percent by weight, the content of B2 is 0.84 to 1.26 percent by weight, and the content of B3 is 0.23 to 3.08 percent by weight.

2. An oxide ion conductor according to claim 1, comprising a plurality of first crystal grains and a plurality of second crystal grains, wherein the first crystal grains comprise elements Ln1, A, and Ga and the second crystal grains comprise element B1, and the first crystal grains and the second crystal grains are present between matrix crystal grains other than the first crystal grains and the second crystal grains.

3. An oxide ion conductor according to claim 1, comprising a plurality of first crystal grains and a plurality of second crystal grains, wherein the first crystal grains comprise elements Ln1, A, and Ga and the second crystal grains comprise element B1, and the first crystal grains and the second crystal grains are present in matrix crystal grains other than the first crystal grains and the second crystal grains.

4. An oxide ion conductor according to claim 2, wherein the grain diameters of the first crystal grains and the second crystal grains are 0.1 to 2.0 μm.

5. An oxide ion conductor according to claim 2, wherein the grain diameter of the matrix crystal grains is 2.0 to 7.0 μm.

6. An oxide ion conductor according to claim 3, wherein the grain diameters of the first crystal grains and the second crystal grains are 0.1 to 2.0 μm.

7. An oxide ion conductor according to claim 3, wherein the grain diameter of the matrix crystal grains is 2.0 to 7.0 μm.

8. The oxide ion conductor of claim 1, wherein B3 is selected from the group consisting of Zn, Mn and Zr.

9. A solid oxide fuel cell comprising an electrolyte comprising an oxide ion conductor according to claim 1.

10. A gas sensor comprising an oxide ion conductor according to claim 1.

11. An oxygen separation membrane comprising an oxide ion conductor according to claim 1.

12. An oxide ion conductor represented by the formula $Ln1_{1-x}A_xGa_{1-y-z-w}B1_yB2_zB3_wO_{3-d}$, wherein Ln1 is at least one element selected from the group consisting of La, Ce, Pr, Nd, and Sm, A is at least one element selected from the group consisting of Sr, Ca, and Ba, B1 is at least one element selected from the group consisting of Mg, Al, and In, B2 is at least one element selected from the group consisting of Co, Fe, Ni, and Cu, B3 is at least one element selected from the group consisting of Al, Mg, Co, Ni, Fe, Cu, Zn, Mn, and Zr, wherein B1, B2 and B3 are different, and x is 0.05 to 0.3, y is 0.025 to 0.29, z is 0.01 to 0.15, w is 0.01 to 0.15, y+z+w is 0.035 to 0.3, and d is 0.04 to 0.3.

13. An oxide ion conductor according to claim 12, comprising a plurality of first crystal grains and a plurality of second crystal grains, wherein the first crystal grains comprise elements Ln1, A, and Ga and the second crystal grains comprise element B1, and the first crystal grains and the second crystal grains are present between matrix crystal grains other than the first crystal grains and the second crystal grains.

14. An oxide ion conductor according to claim 12, comprising a plurality of first crystal grains and a plurality of second crystal grains, wherein the first crystal grains comprise elements Ln1, A, and Ga and the second crystal grains comprise element B1, and the first crystal grains and the second crystal grains are present in matrix crystal grains other than the first crystal grains and the second crystal grains.

15. An oxide ion conductor according to claim 13, wherein the grain diameters of the first crystal grains and the second crystal grains are 0.1 to 2.0 μm.

16. An oxide ion conductor according to claim 13, wherein the grain diameter of the matrix crystal grains is 2.0 to 7.0 μm.

17. An oxide ion conductor according to claim 14, wherein the grain diameters of the first crystal grains and the second crystal grains are 0.1 to 2.0 μm.

18. An oxide ion conductor according to claim 14, wherein the grain diameter of the matrix crystal grains is 2.0 to 7.0 μm.

19. The oxide ion conductor of claim 12, wherein B3 is selected from the group consisting of Zn, Mn and Zr.

20. A solid oxide fuel cell comprising an electrolyte comprising an oxide ion conductor according to claim 12.

21. A gas sensor comprising an oxide ion conductor according to claim 12.

22. An oxygen separation membrane comprising an oxide ion conductor according to claim 12.

23. A method comprising:

mixing individual powdered oxides comprising Ln1, A, Ga, B1, and B2 to form a first powdered mixture;

calcining the first powdered mixture at 500 to 1,300 C. for 1 to 10 hours to form a calcined powder;

mixing a powdered oxide comprising B3 with the calcined powder to form a second powdered mixture;

molding the second powdered mixture into a molded body having a predetermined shape; and baking the molded body at 1,200 to 1,600 C for 0.5 to 20 hours to form an oxide ion conductor of formula Ln1AGaB1B2B3O wherein Ln1 is at least one element selected from the group consisting of La, Ce, Pr, Nd, and Sm, the content thereof being 43.6 to 51.2 percent by weight, A is at least one element selected from the group consisting of Sr, Ca, and Ba, the content thereof being 5.4 to 11.1 percent by weight, the content of Ga is 20.0 to 23.9 percent by weight, B1 is at least one element selected from the group consisting of Mg, Al, and In, B2 is at least one element selected from the group consisting of Co, Fe, Ni, and Cu, B3 is at least one element selected from the group consisting Al, Mg, Co, Ni, Fe, Cu, Zn, Mn, and Zr, wherein B3 is an element different from B1 and B2, the content of B1 is 1.21 to 1.76 percent by weight, the content of B2 is 0.84 to 1.26 percent by weight, and the content of B3 is 0.23 to 3.08 percent by weight.

* * * * *